United States Patent
Lareau

(10) Patent No.: US 9,895,524 B2
(45) Date of Patent: Feb. 20, 2018

(54) FLUID BYPASS DEVICE FOR VALVED CATHETERS

(71) Applicant: AngioDynamics, Inc., Latham, NY (US)

(72) Inventor: Raymond J Lareau, Westford, MA (US)

(73) Assignee: AngioDynamics, Inc., Latham, NY (US)

( * ) Notice: Subject to any disclaimer, the term of this patent is extended or adjusted under 35 U.S.C. 154(b) by 803 days.

(21) Appl. No.: 13/941,745

(22) Filed: Jul. 15, 2013

(65) Prior Publication Data
US 2014/0163516 A1  Jun. 12, 2014

Related U.S. Application Data

(60) Provisional application No. 61/671,226, filed on Jul. 13, 2012.

(51) Int. Cl.
*A61M 39/10* (2006.01)
*A61B 5/0402* (2006.01)
(Continued)

(52) U.S. Cl.
CPC ........... *A61M 39/10* (2013.01); *A61B 5/0215* (2013.01); *A61B 5/0245* (2013.01);
(Continued)

(58) Field of Classification Search
CPC ............ A61M 39/045; A61M 39/0693; A61M 39/10; A61M 39/22; A61M 2039/064;
(Continued)

(56) References Cited

U.S. PATENT DOCUMENTS

| 2,446,571 A | 8/1948 | Browne |
| 2,720,881 A | 10/1955 | Jones |

(Continued)

FOREIGN PATENT DOCUMENTS

| CN | 102155808 | 8/2017 |
| DE | 3048203 | 7/1982 |

(Continued)

OTHER PUBLICATIONS

Moureau, Nancy L., Glenda L. Dennis, Elizabeth Ames, and Robyn Severe. "Electrocardiogram (EKG) Guided Peripherally Inserted Central Catheter Placement and Tip Position: Results of a Trial to Replace Radiological Confirmation." Journal of the Association for Vascular Access 15.1 (2010): 8-14. Web.*

(Continued)

*Primary Examiner* — Imani Hayman
*Assistant Examiner* — James D Ponton
(74) *Attorney, Agent, or Firm* — Peter Flora, Esq.

(57) ABSTRACT

Bypass elements for medical valves and methods of using the same are disclosed. Embodiments of the invention include an insert having a tip that is adapted to displace a valve element without penetrating it, and a lumen that fluidly communicates with a lumen of a valve housing distal to the valve element when the bypass element is engaged. Bypass elements are used, in certain embodiments, to facilitate fluid pressure and ECG signal measurements through implanted medical devices including catheters.

12 Claims, 9 Drawing Sheets

(51) Int. Cl.
    *A61B 5/0215*     (2006.01)
    *A61B 5/0245*     (2006.01)
    *A61M 39/06*     (2006.01)
    *A61M 39/04*     (2006.01)
    *A61M 39/26*     (2006.01)
    *A61M 39/24*     (2006.01)
    *A61M 25/00*     (2006.01)
    *A61M 39/22*     (2006.01)

(52) U.S. Cl.
    CPC ......... *A61B 5/0402* (2013.01); *A61M 39/045*
    (2013.01); *A61M 39/0693* (2013.01); *A61M*
    *39/26* (2013.01); *A61M 25/0097* (2013.01);
    *A61M 39/221* (2013.01); *A61M 2039/064*
    (2013.01); *A61M 2039/1072* (2013.01); *A61M*
    *2039/2426* (2013.01)

(58) Field of Classification Search
    CPC ............. A61M 2039/2426; A61B 5/02; A61B
        5/0215; A61B 5/0235; A61B 5/0245;
        A61B 5/04; A61B 5/0402
    USPC ........................................................ 604/247
    See application file for complete search history.

(56) References Cited

U.S. PATENT DOCUMENTS

| | | |
|---|---|---|
| 2,755,060 A | 7/1956 | Twyman |
| 3,113,586 A | 12/1963 | Edmark |
| 3,159,175 A | 12/1964 | Macmillan |
| 3,159,176 A | 12/1964 | Gifford et al. |
| 3,477,438 A | 11/1969 | Allen et al. |
| 3,514,438 A | 5/1970 | Bixler et al. |
| 3,525,357 A | 8/1970 | Koreski |
| 3,621,557 A | 11/1971 | Cushman et al. |
| 3,669,323 A | 11/1971 | Cushman |
| 3,673,612 A | 7/1972 | Merrill et al. |
| 3,674,183 A | 7/1972 | Venable et al. |
| 3,710,942 A | 1/1973 | Rosenberg |
| 3,788,327 A | 1/1974 | Donowitz et al. |
| 3,811,466 A | 5/1974 | Ohringer |
| 3,848,579 A | 11/1974 | Villa-Real |
| 3,941,149 A | 3/1976 | Mittleman |
| 3,955,594 A | 5/1976 | Snow |
| 4,072,146 A | 2/1978 | Howes |
| 1,142,525 A | 3/1979 | Binard et al. |
| 4,143,853 A | 3/1979 | Abramson |
| 1,244,379 A | 1/1981 | Smith |
| 4,387,879 A | 6/1983 | Tauschinski |
| 4,405,316 A | 9/1983 | Mittleman |
| 4,434,810 A | 3/1984 | Atkinson |
| 4,447,237 A | 5/1984 | Frisch et al. |
| 4,468,224 A | 8/1984 | Enzmann et al. |
| 4,502,502 A | 3/1985 | Krug |
| 4,524,805 A | 6/1985 | Hoffman |
| 4,543,087 A | 9/1985 | Sommercorn et al. |
| 4,552,553 A | 11/1985 | Schulte et al. |
| 4,610,665 A | 9/1986 | Matsumoto et al. |
| 4,616,768 A | 10/1986 | Flier |
| 4,646,945 A | 3/1987 | Steiner et al. |
| 4,673,393 A | 6/1987 | Suzuki et al. |
| 4,681,572 A | 7/1987 | Tokarz et al. |
| 4,692,146 A | 9/1987 | Hilger |
| 4,722,725 A | 2/1988 | Sawyer et al. |
| 4,790,832 A | 12/1988 | Lopez |
| 4,798,594 A | 1/1989 | Hillstead |
| 4,801,297 A | 1/1989 | Mueller |
| 4,842,591 A * | 6/1989 | Luther ............... A61M 39/0693 285/3 |
| 4,908,028 A | 3/1990 | Colon et al. |
| 4,944,726 A | 7/1990 | Hilal et al. |
| 4,946,448 A | 8/1990 | Richmond |
| 4,960,412 A | 10/1990 | Fink |
| 4,991,745 A | 2/1991 | Brown |
| 5,000,745 A | 3/1991 | Guest et al. |
| 5,009,391 A | 4/1991 | Steigerwald |
| 5,030,210 A | 7/1991 | Alchas |
| 5,084,015 A | 1/1992 | Moriuchi |
| 5,098,405 A | 3/1992 | Peterson et al. |
| 5,125,893 A | 6/1992 | Dryden |
| 5,143,853 A | 9/1992 | Walt |
| 5,147,332 A | 9/1992 | Moorehead |
| 5,149,327 A | 9/1992 | Oshiyama |
| 5,167,638 A | 12/1992 | Felix et al. |
| 5,169,393 A | 12/1992 | Moorehead et al. |
| 5,176,652 A | 1/1993 | Littrell |
| 5,176,662 A | 1/1993 | Bartholomew et al. |
| 5,201,722 A | 4/1993 | Moorehead et al. |
| 5,205,834 A | 4/1993 | Moorehead et al. |
| 5,215,538 A * | 6/1993 | Larkin .................. A61M 39/26 137/516.13 |
| 5,249,598 A | 10/1993 | Schmidt |
| 5,253,765 A | 10/1993 | Moorehead et al. |
| 5,254,086 A | 10/1993 | Palmer et al. |
| 5,255,676 A | 10/1993 | Russo |
| 5,324,274 A | 6/1994 | Martin |
| 5,330,424 A | 7/1994 | Palmer et al. |
| 5,336,203 A | 8/1994 | Goldhardt et al. |
| 5,360,407 A | 11/1994 | Leonard et al. |
| 5,370,624 A | 12/1994 | Edwards et al. |
| 5,395,352 A | 3/1995 | Penny |
| 5,396,925 A | 3/1995 | Poli |
| 5,399,168 A | 3/1995 | Wadsworth, Jr. et al. |
| 5,401,255 A | 3/1995 | Sutherland et al. |
| D357,735 S | 4/1995 | McPhee |
| 5,405,340 A | 4/1995 | Fageol et al. |
| 5,411,491 A | 5/1995 | Goldhardt et al. |
| 5,453,097 A | 9/1995 | Paradis |
| 5,454,784 A | 10/1995 | Atkinson et al. |
| 5,469,805 A | 11/1995 | Gibbs |
| 5,470,305 A | 11/1995 | Arnett et al. |
| 5,484,420 A | 1/1996 | Russo |
| 5,542,923 A | 8/1996 | Ensminger et al. |
| 5,545,150 A | 8/1996 | Danks et al. |
| 5,554,136 A | 9/1996 | Luther |
| 5,562,618 A | 10/1996 | Cai et al. |
| 5,571,093 A | 11/1996 | Cruz et al. |
| 5,575,769 A | 11/1996 | Vaillancourt |
| 5,624,395 A | 4/1997 | Mikhail et al. |
| 5,637,099 A | 6/1997 | Durdin et al. |
| 5,667,500 A | 9/1997 | Palmer et al. |
| 5,707,357 A | 1/1998 | Mikhail et al. |
| 5,743,873 A | 4/1998 | Cai et al. |
| 5,743,884 A | 4/1998 | Hasson et al. |
| 5,743,894 A | 4/1998 | Swisher |
| 5,752,928 A | 5/1998 | de Roulhac et al. |
| 5,752,938 A | 5/1998 | Flatland et al. |
| 5,769,107 A * | 6/1998 | Woodruff ............ B67D 7/0294 137/1 |
| 5,803,078 A | 9/1998 | Brauner |
| 5,807,349 A | 9/1998 | Person et al. |
| 5,810,789 A | 9/1998 | Powers et al. |
| 5,843,044 A | 12/1998 | Moorehead |
| 5,853,397 A | 12/1998 | Shemesh et al. |
| 5,858,003 A * | 1/1999 | Atala ................. A61M 25/0017 604/175 |
| 5,865,308 A | 2/1999 | Qin et al. |
| 5,944,698 A | 8/1999 | Fischer et al. |
| 5,984,902 A | 11/1999 | Moorehead |
| 5,989,233 A | 11/1999 | Yoon |
| 6,033,393 A | 3/2000 | Balbierz et al. |
| 6,045,734 A | 4/2000 | Luther et al. |
| 6,050,934 A | 4/2000 | Mikhail et al. |
| 6,056,717 A | 5/2000 | Finch et al. |
| 6,062,244 A | 5/2000 | Arkans |
| 6,092,551 A | 7/2000 | Bennett |
| 6,099,505 A | 8/2000 | Ryan et al. |
| 6,120,483 A | 9/2000 | Davey et al. |
| 6,152,129 A | 11/2000 | Berthon-Jones |
| 6,152,909 A | 11/2000 | Bagaoisan et al. |
| 6,167,886 B1 | 1/2001 | Engel et al. |
| 6,210,366 B1 | 4/2001 | Sanfilippo, II |
| 6,227,200 B1 | 5/2001 | Crump et al. |

(56) References Cited

U.S. PATENT DOCUMENTS

| | | |
|---|---|---|
| 6,270,489 B1 | 8/2001 | Wise et al. |
| 6,306,124 B1 | 10/2001 | Jones et al. |
| 6,364,861 B1 | 4/2002 | Feith et al. |
| 6,364,867 B2 | 4/2002 | Wise et al. |
| 6,375,637 B1 | 4/2002 | Campbell et al. |
| 6,436,077 B1 | 8/2002 | Davey et al. |
| 6,442,415 B1 | 8/2002 | Bis et al. |
| 6,446,671 B2 | 9/2002 | Armenia et al. |
| 6,508,791 B1 | 1/2003 | Guerrero |
| 6,551,270 B1 | 4/2003 | Bimbo et al. |
| 6,610,031 B1 | 8/2003 | Chin |
| 6,726,063 B2 | 4/2004 | Stull et al. |
| 6,786,884 B1 | 9/2004 | DeCant, Jr. et al. |
| 6,874,999 B2 | 4/2005 | Dai et al. |
| 6,929,631 B1 | 8/2005 | Brugger et al. |
| 6,953,450 B2 | 10/2005 | Baldwin et al. |
| 6,994,314 B2 | 2/2006 | Garnier et al. |
| 7,025,744 B2 * | 4/2006 | Utterberg ............. A61M 39/02 604/256 |
| 7,081,106 B1 | 7/2006 | Guo et al. |
| 7,252,652 B2 | 8/2007 | Moorehead et al. |
| 7,291,133 B1 | 11/2007 | Kindler et al. |
| 7,316,655 B2 | 1/2008 | Garibotto et al. |
| 7,435,236 B2 | 10/2008 | Weaver et al. |
| D595,846 S | 7/2009 | Racz et al. |
| D596,288 S | 7/2009 | Racz et al. |
| 7,601,141 B2 | 10/2009 | Dikeman et al. |
| 7,637,893 B2 | 12/2009 | Christensen et al. |
| 7,713,250 B2 | 5/2010 | Harding et al. |
| 7,731,700 B1 | 6/2010 | Schytte |
| 7,758,541 B2 | 7/2010 | Wallace et al. |
| 7,931,619 B2 | 4/2011 | Diamond et al. |
| 7,947,032 B2 | 5/2011 | Harding et al. |
| 7,951,121 B2 | 5/2011 | Weaver et al. |
| 7,988,679 B2 | 8/2011 | Daly et al. |
| 7,993,327 B2 | 8/2011 | Casey, II |
| D644,731 S | 9/2011 | Fangrow, Jr. |
| 8,034,035 B2 | 10/2011 | Weaver et al. |
| 8,079,987 B2 | 12/2011 | Moorehead et al. |
| 8,083,721 B2 | 12/2011 | Miller |
| 8,105,314 B2 | 1/2012 | Fangrow, Jr. |
| 8,187,234 B2 | 5/2012 | Weaver et al. |
| 8,257,321 B2 | 9/2012 | Lareau et al. |
| 8,328,768 B2 | 12/2012 | Quigley et al. |
| 8,337,470 B2 | 12/2012 | Prasad et al. |
| 8,343,113 B2 | 1/2013 | Hokanson |
| 8,377,011 B2 | 2/2013 | Weaver et al. |
| 8,398,607 B2 | 3/2013 | Fangrow, Jr. |
| 8,444,628 B2 | 5/2013 | Fangrow, Jr. |
| 8,454,574 B2 | 6/2013 | Weaver et al. |
| 8,454,579 B2 | 6/2013 | Fangrow, Jr. |
| 8,523,821 B2 | 9/2013 | Miller |
| 8,529,523 B2 | 9/2013 | Weaver et al. |
| 8,540,685 B2 | 9/2013 | Moorehead et al. |
| 8,585,660 B2 | 11/2013 | Murphy |
| 8,603,070 B1 | 12/2013 | Lareau et al. |
| 8,628,515 B2 | 1/2014 | Fangrow, Jr. |
| 8,679,074 B2 | 3/2014 | Daly et al. |
| 8,726,931 B2 | 5/2014 | Buiser et al. |
| 8,753,320 B2 | 6/2014 | Miller |
| 8,758,306 B2 | 6/2014 | Lopez et al. |
| 8,784,402 B1 | 7/2014 | Lareau et al. |
| 8,789,558 B2 | 7/2014 | Volker |
| 8,870,850 B2 | 10/2014 | Fangrow, Jr. |
| 8,876,797 B2 | 11/2014 | Lareau et al. |
| 8,926,571 B1 | 1/2015 | Keith |
| D722,155 S | 2/2015 | Wiegel et al. |
| D722,156 S | 2/2015 | Wiegel et al. |
| D722,157 S | 2/2015 | Wiegel et al. |
| 9,044,541 B2 | 6/2015 | Blanchard et al. |
| 9,186,494 B2 | 11/2015 | Fangrow |
| 9,192,753 B2 | 11/2015 | Lopez et al. |
| 9,192,755 B2 | 11/2015 | Ravenscroft |
| 9,205,243 B2 | 12/2015 | Lopez et al. |
| 9,206,283 B1 | 12/2015 | Santerre et al. |
| 9,238,129 B2 | 1/2016 | Fangrow, Jr. |
| 9,278,206 B2 | 3/2016 | Fangrow |
| D757,259 S | 5/2016 | Duck et al. |
| 2001/0023333 A1 | 9/2001 | Wise et al. |
| 2001/0037079 A1 | 11/2001 | Burbank et al. |
| 2002/0010425 A1 | 1/2002 | Guo et al. |
| 2002/0016584 A1 | 2/2002 | Wise et al. |
| 2002/0111662 A1 * | 8/2002 | Iaizzo ............. A61B 5/0215 607/119 |
| 2002/0121530 A1 | 9/2002 | Socier |
| 2002/0156430 A1 | 10/2002 | Haarala et al. |
| 2002/0157664 A1 | 10/2002 | Fugelsang et al. |
| 2002/0165492 A1 | 11/2002 | Davey et al. |
| 2002/0193752 A1 | 12/2002 | Lynn |
| 2003/0122095 A1 | 7/2003 | Wilson et al. |
| 2004/0034324 A1 | 2/2004 | Seese et al. |
| 2004/0064128 A1 | 4/2004 | Raijman et al. |
| 2004/0102738 A1 | 5/2004 | Dikeman et al. |
| 2004/0108479 A1 | 6/2004 | Gamier et al. |
| 2004/0186444 A1 | 9/2004 | Daly et al. |
| 2004/0193119 A1 | 9/2004 | Canaud et al. |
| 2004/0210194 A1 | 10/2004 | Bonnette et al. |
| 2004/0267185 A1 | 12/2004 | Weaver et al. |
| 2005/0010176 A1 | 1/2005 | Dikeman et al. |
| 2005/0027261 A1 | 2/2005 | Weaver et al. |
| 2005/0043703 A1 | 2/2005 | Nordgren |
| 2005/0049555 A1 | 3/2005 | Moorehead et al. |
| 2005/0149116 A1 | 7/2005 | Edwards et al. |
| 2005/0165364 A1 | 7/2005 | DiMatteo et al. |
| 2005/0171488 A1 | 8/2005 | Weaver et al. |
| 2005/0171490 A1 | 8/2005 | Weaver et al. |
| 2005/0171510 A1 | 8/2005 | DiCarlo et al. |
| 2005/0283122 A1 | 12/2005 | Nordgren |
| 2006/0129092 A1 | 6/2006 | Hanlon et al. |
| 2006/0135949 A1 | 6/2006 | Rome et al. |
| 2006/0149189 A1 | 7/2006 | Diamond et al. |
| 2006/0149211 A1 | 7/2006 | Simpson et al. |
| 2006/0149214 A1 | 7/2006 | Breiter et al. |
| 2007/0161940 A1 | 7/2007 | Blanchard et al. |
| 2007/0161970 A1 | 7/2007 | Spohn et al. |
| 2007/0276313 A1 | 11/2007 | Moorehead et al. |
| 2008/0097341 A1 | 4/2008 | Casey |
| 2008/0108956 A1 | 5/2008 | Lynn et al. |
| 2009/0177187 A1 | 7/2009 | Heaver et al. |
| 2009/0292252 A1 | 11/2009 | Lareau et al. |
| 2011/0087093 A1 | 4/2011 | Buiser |
| 2011/0118612 A1 * | 5/2011 | Miller ............. A61B 5/0215 600/486 |
| 2011/0264054 A1 | 10/2011 | Miller |
| 2011/0313367 A1 | 12/2011 | Daly et al. |
| 2011/0313368 A1 | 12/2011 | Weaver et al. |
| 2012/0271247 A1 | 10/2012 | Weaver et al. |
| 2012/0325351 A1 | 12/2012 | Volker |
| 2013/0060200 A1 | 3/2013 | Dalton et al. |
| 2013/0220462 A1 | 8/2013 | Lareau et al. |
| 2013/0338608 A1 | 12/2013 | Moorehead et al. |
| 2014/0081285 A1 | 3/2014 | Kucklick |
| 2014/0163516 A1 | 6/2014 | Lareau |
| 2015/0135554 A1 | 5/2015 | Smith |
| 2016/0008530 A1 | 1/2016 | Weaver et al. |
| 2016/0121041 A1 | 5/2016 | Weaver et al. |

FOREIGN PATENT DOCUMENTS

| | | |
|---|---|---|
| DE | 20208420 | 10/2002 |
| EP | 0128525 | 12/1984 |
| EP | 0198962 | 10/1986 |
| EP | 0337617 | 10/1989 |
| EP | 0366814 | 5/1990 |
| EP | 0474069 | 3/1992 |
| EP | 0864336 | 9/1998 |
| EP | 0882466 | 12/1998 |
| EP | 0930082 | 7/1999 |
| EP | 1016431 | 7/2000 |
| EP | 0128525 NO | 5/2016 |
| FR | 2508008 NO | 12/1982 |
| FR | 2718969 | 10/1995 |
| GB | 2102398 | 2/1983 |
| WO | WO9206732 | 4/1992 |

(56) References Cited

FOREIGN PATENT DOCUMENTS

| WO | WO9516480 | 6/1995 |
|---|---|---|
| WO | WO9617190 | 6/1996 |
| WO | WO9623158 | 8/1996 |
| WO | WO9723255 | 7/1997 |
| WO | WO9726931 | 7/1997 |
| WO | WO9822178 | 5/1998 |
| WO | WO9942166 | 8/1998 |
| WO | WO0006230 | 2/2000 |
| WO | WO0044419 | 8/2000 |
| WO | WO03084832 | 10/2003 |
| WO | WO2005023355 | 3/2005 |
| WO | WO2008051647 | 5/2008 |
| WO | WO2009112838 | 9/2009 |
| WO | WO2011008689 | 1/2011 |
| WO | WO2011062767 | 5/2011 |
| WO | WO2014014602 | 1/2014 |

OTHER PUBLICATIONS

Hoffer et al., Prospective Randomized Comparison of Valved Versus Nonvalved Peripherally Inserted Central Vein Catheters, (Oct. 1999), pp. 1393-1398.

Biffi, et al., A Randomized, Prospective Trial of Central Venous Ports Connected to Standard Open-Ended or Groshong Catheters in Adult Oncology Patients, American Cancer Society, (Sep. 1, 2001), pp. 1204-1212.

Hoffer et al., Peripherally Inserted Central Catheters with Distal versus Proximal Valves: Prospective Randomized Trial, Society of Interventional Radiology, (Oct. 2001), pp. 1173-1177, vol. 12 No. 10.

McMahon, Evaluating New Technology to Improve Patient Outcomes, (Jul. 2002), pp. 250-255, vol. 25, No. 4.

Carlo et al., A prospective Randomized Trial Demonstrating Valved Implantable Ports Have Fewer Complications and Lower Overall Cost Than Nonvalved Implantable Ports, (Aug. 7, 2004), pp. 722-727.

Burns, The Vanderbilt PICC Service: Program, Procedural, and Patient Outcomes Successes, (2005), pp. 1-10, vol. 10 No. 4.

Ricchezza et al., A Strategy for Reducing Catheter Occlusions and Infections: The Experience at St. Joseph's Hospital, (2009).

Ong et al., Prospective Randomized Comparative Evaluation of Proximal Valve Polyurethane and Distal Valve Silicone Peripherally Inserted Central Catheters, (Aug. 2010), 1191-1196.

Aw et al., Incidence and Predictive Factors of Symptomatic Thrombosis Related to Peripherally Inserted Central Catheters in Chemotherapy Patients, (2012), pp. 323-326.

Johnston et al., The Effect of Peripherally Inserted Central Catheter (PICC) Valve Technology on Catheter Occlusion Rates—The 'ELeCTRiC' Study, (2012), pp. 421-425.

International Search Report PCT-US-05-011244_ISR dated Jun. 6, 2005.

International Search Report PCT-US-05-000761_ISR dated Dec. 4, 2005.

International Search Report PCT-US-05-000761_WOSA dated Jul. 29, 2006.

International Search Report PCT-US-05-000761_IPRP dated Jul. 31, 2006.

International Search Report PCT-US-05-001244_IPRP dated Jul. 31, 2006.

International Search Report PCT-US-09-044468_ISR dated Dec. 23, 2009.

International Search Report PCT-US-10-041698_ISR dated Dec. 2010.

International Search Report PCT-US-09-044468_IPRP dated Nov. 23, 2010.

International Search Report PCT-US-09-044468_WOSA dated Nov. 25, 2010.

International Search Report 11158827_ESR dated May 11, 2011.

International Search Report PCT-US10-041698_IPRP dated Nov. 17, 2012.

International Search Report 11158827-3_ESO dated May 19, 2011.

\* cited by examiner

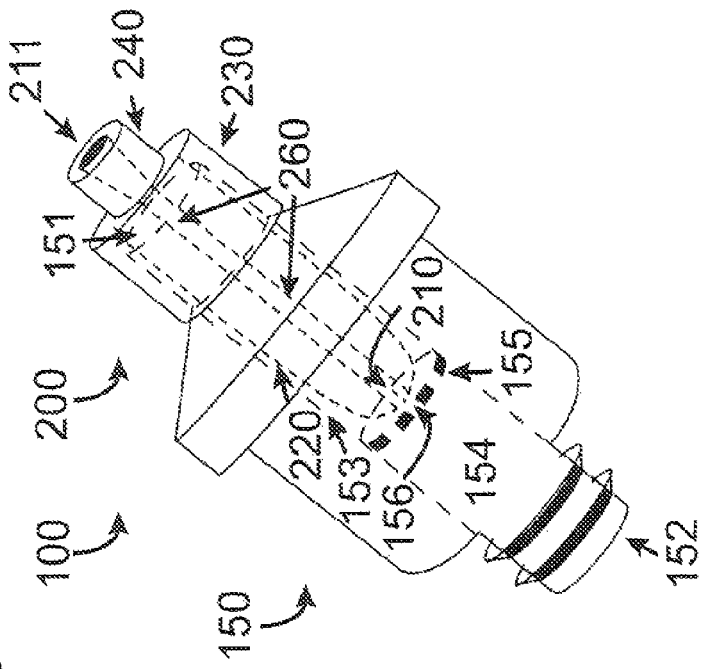
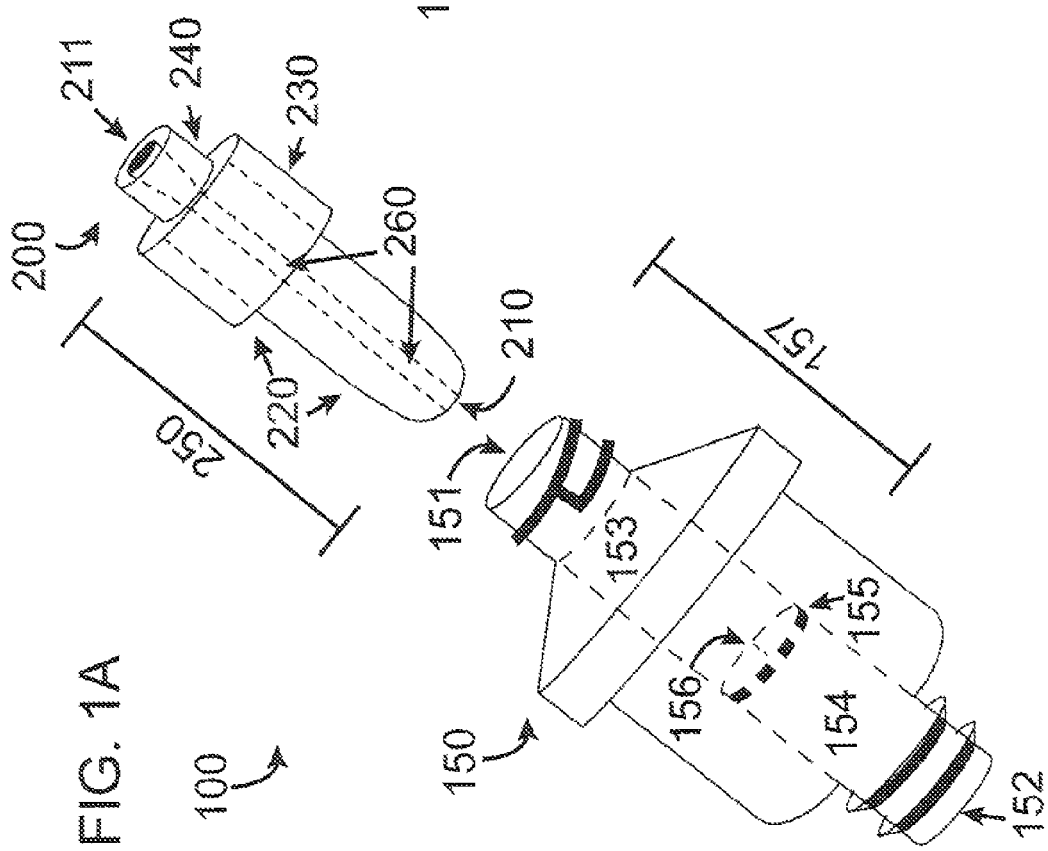

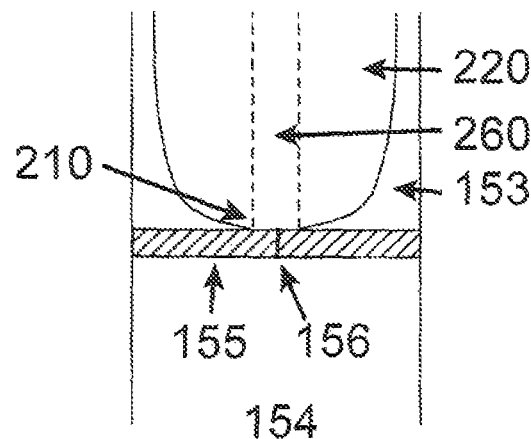
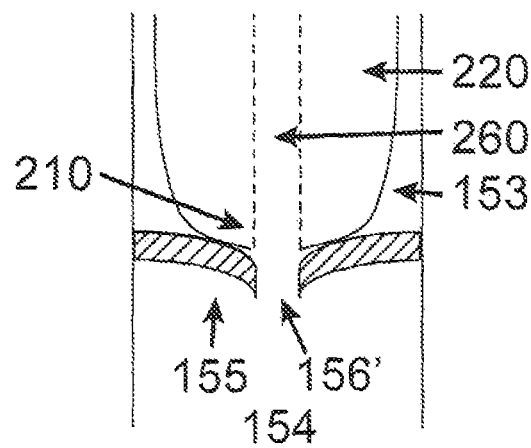

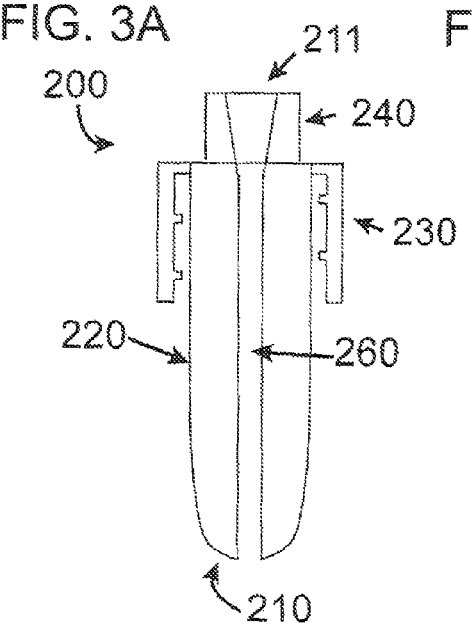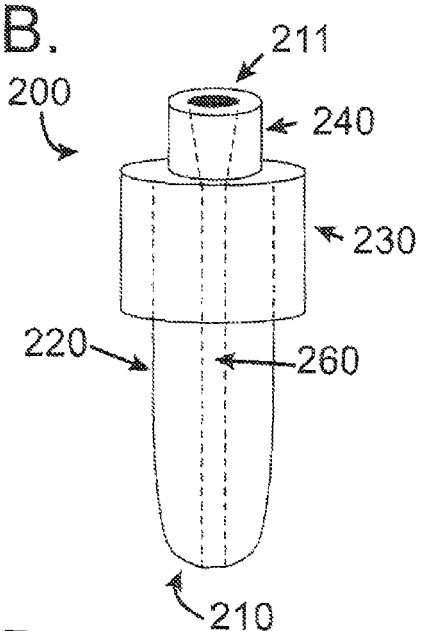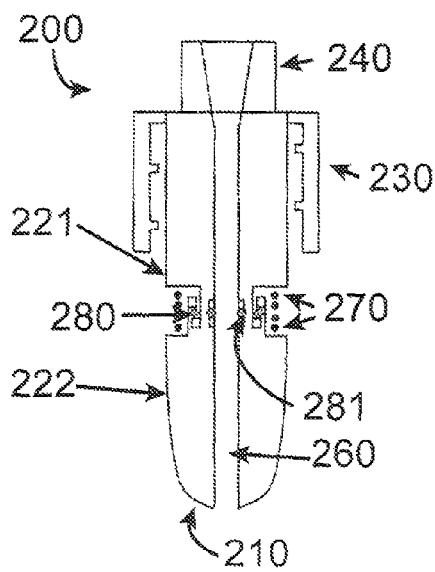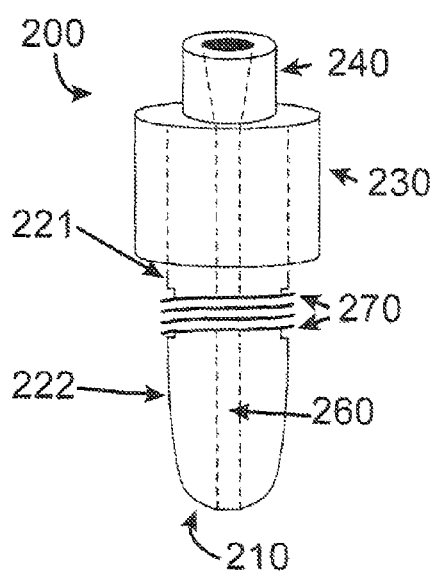

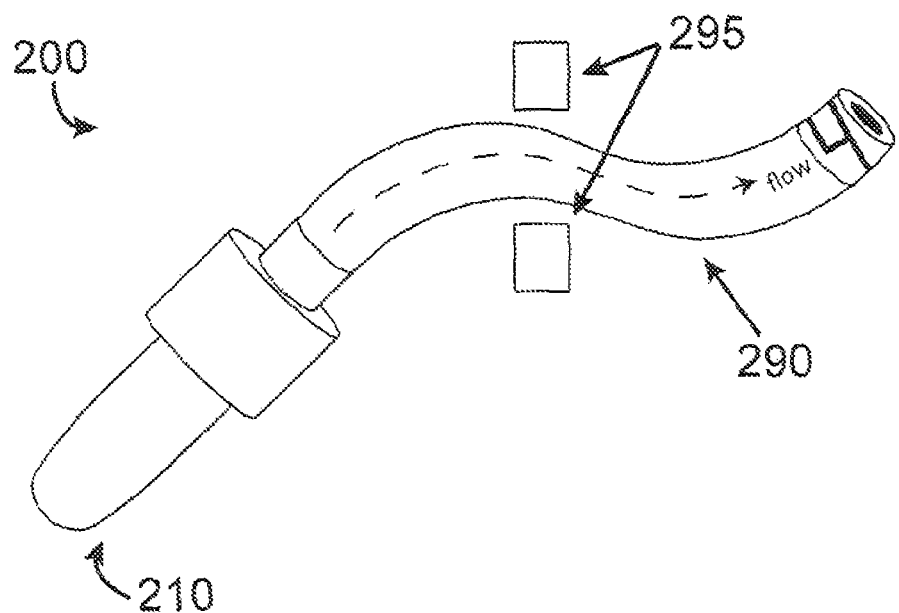
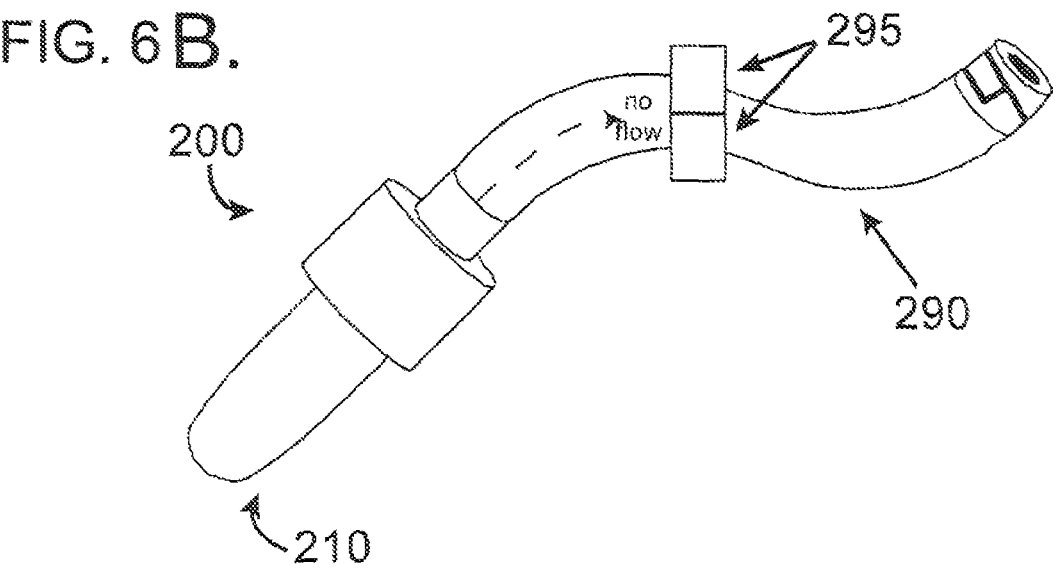

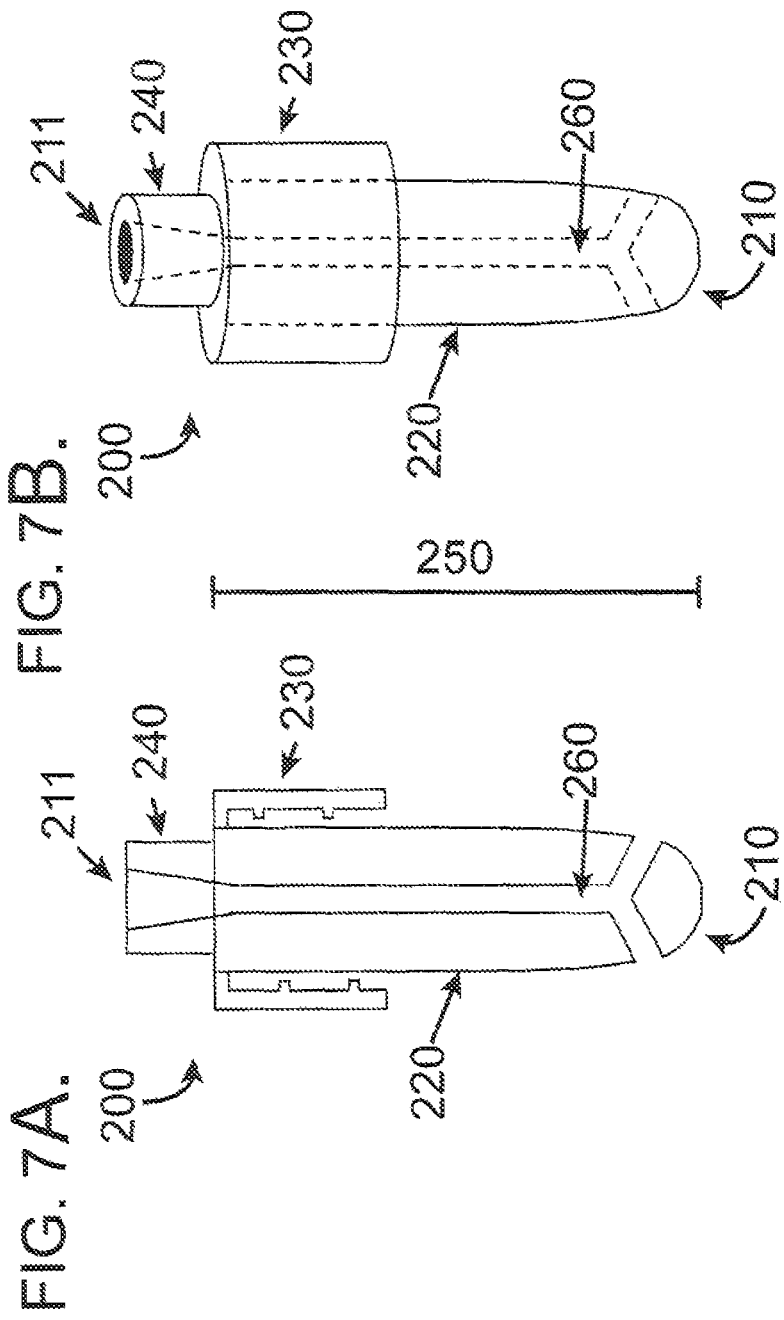

FLUID BYPASS DEVICE FOR VALVED CATHETERS

TECHNICAL FIELD

The present invention relates to systems and methods for transmission and measurement of fluid through valved catheters.

BACKGROUND

There are a number of implantable medical devices used for the repeated and prolonged access to a patients vascular system or other bodily conduits. Such devices include peripherally-inserted central catheters ("PICC's"), central venous catheters ("CVC's"), dialysis catheters, implantable ports, and midline infusion catheters. These devices are typically implanted into a patient for an extended period of time to allow for multiple treatments, such as the delivery of therapeutic agents or dialysis treatments. Use of such devices eliminates the need for multiple placements of single-use devices, thus reducing the risk of infection and placement complications, and reducing the overall cost of patient care. Examples of such implantable medical devices include BioFlo™ PICC's, Vaxcer® PICC's, Xcela® PICC's, and Vaxcel® Plus Chronic Dialysis catheters (all from AngioDynamics, Inc., Latham, N.Y.). Implantable devices such as these have distal sections that reside within the vasculature, and proximal sections that are typically outdwelling and include luers for connection to fluid sources and other medical devices.

Because these devices remain in a patient's body for an extended period of time, it is common practice to seal their proximal ends between uses to prevent blood loss and infection. Such a seal may be created with the use of a simple clamp placed on the catheter line (e.g. the Morpheus® SMART PICC, AngioDynamics, Inc., Latham, N.Y.), or with the use of an in-line valve such as that found in the Vaxcel® PICC with PASV® Valve Technology and described in U.S. Pat. Nos. 5,205,834 and 7,252,652, which are incorporated herein by reference. In-line valves are pressure activated such that they open to allow for fluid to be delivered through the valve upon the application of some threshold pressure, above which the valve will open, and below which the valve remains closed. Pressure activated valves may advantageously prevent patient complications and infections. In line catheter valves typically include a valve housing that defines a lumen (referred to as the "valve lumen") and a valve element disposed across the valve lumen to regulate fluid flow. The valve element is normally closed, but opens in response to pressures above a predefined threshold. Valve elements used in in-line catheter valves are typically flexible slitted membranes such as those disclosed in U.S. Pat. No. 5,843,044, which is incorporated by reference herein.

It is often desirable to measure fluid pressures such as blood pressure or central venous pressure through a catheter. It may also be desirable to measure an ECG signal through a column of saline extending from a distal catheter tip to a proximal extension tube and luer. In the case of valved devices, however, the in-line valve inhibits transmission of fluid pressure from the distal catheter tip to the proximal luer. Current practice is to insert an elongated instrument through the valve element (typically a slitted membrane), but the insertion of elongated tools into the valve lumen to measure blood pressure raises a risk of puncturing the membrane or tearing, weakening, or otherwise permanently deforming the membrane or its slits. Additionally, excessive displacement of the edges of slit raises the risk that the edges will not return to their fully closed, fully and flushly apposed positions, instead returning to a folded or puckered position, and that gaps or edges may exist through which fluids may leak, potentially leading to thrombosis and/or infection. Accordingly, there is a need for systems that permit the measurement of blood pressure through catheters having in-line valves, preferably without the risk of damaging the valve element.

SUMMARY OF THE INVENTION

The need described above is met by the present invention, which relates in one aspect to a bypass element for a valve which opens but does not penetrate the valve element, permitting fluid communication across the valve element. In certain embodiments, the insert includes an insert tip that displaces one or more edges of a slit in a membrane without penetrating the slit, as well as an insert connector connectable to a measurement device, which is in fluid communication with the insert tip via an insert lumen that permits fluid flow between the insert tip and the insert connector. The insert may have an outer diameter sized to fit within the valve lumen. In various embodiments, the insert is longitudinally compressible by means of a distal portion that includes the insert tip, a proximal portion that includes the connector, and a compressible element disposed at a junction of the proximal and distal portions. The proximal and distal portions can optionally rotate relative to one another, and the insert optionally includes a sealing member disposed at the junction of the proximal and distal portions to prevent leakage into or out of the insert lumen at the junction of the proximal and distal insert portions.

In another aspect, the invention relates to a system for measurement that includes a catheter insertable into a patient, including a valve housing with a valve lumen and a flexible slitted membrane positioned in the valve lumen which membrane remains closed under pressures below a threshold value, and an insert that includes an insert section that fits inside the valve lumen and opens the slit, as well as a proximal connector that can be engaged with the catheter and an insert lumen that runs between the insert tip and the insert connector and permits fluid flow between them. In certain embodiments the insert is longitudinally compressible by means of a distal portion that includes the insert tip, a proximal portion that includes the connector, and a compressible element disposed at a junction of the proximal and distal portions. The proximal and distal portions can optionally rotate relative to one another, and the insert optionally includes a sealing member to prevent leakage into or out of the insert lumen at the junction of the proximal and distal portions.

In yet another aspect, the invention relates to a method of measuring a physical characteristic in a patient with a catheter having a pressure activated valve that, in turn, utilizes a membrane with at least one slit, which slit opens in response to a fluid pressure in excess of a predetermined threshold, as a valve element. The method includes, in various embodiments, providing an insert that has a section which fits inside the valve lumen, contacts the membrane and opens the slit without penetrating it, as well as a proximal connector that can be engaged with the catheter and an insert lumen that runs between the insert tip and the insert connector and permits fluid flow between them. The method also includes placing the insert into the valve housing to permit fluid transmission between the catheter and the insert lumen through the open slit. The physical characteristic may be selected from the group consisting of pressure waves, acoustic waves and ECG waves, and the method may also include one or more of the steps of determining the position of the distal tip of the catheter based on the measured wave, and optionally repositioning the distal tip of the catheter based on the measurements to achieve targeted tip position. The method may also include positioning the distal tip of the catheter in an optimal position during initial insertion of the catheter.

DESCRIPTION OF THE DRAWINGS

The figures provided herein are not necessarily drawn to scale, with emphasis being placed on illustration of the principles of the invention.

FIG. 1A includes a side view of an insert and a pressure activated valve in accordance with certain embodiments of the invention, and FIG. 1B includes a side view of an insert inserted into a pressure activated valve in accordance with certain embodiments of the invention.

FIGS. 2A and 2B include a side view of an insert positioned within a pressure activated valve in accordance with certain embodiments of the invention.

FIGS. 3A and 3C include valve inserts in cross-section views according to certain embodiments of the invention. FIGS. 3B and 3D include valve inserts in perspective views according to certain embodiments of the invention.

FIGS. 6A and 6B include a side view of an insert having an extension tube according to certain embodiments of the invention.

FIGS. 7A and 7B include side and cross-sectional views of inserts having branching insert lumens according to certain embodiments of the invention.

DETAILED DESCRIPTION

Figure 4A:
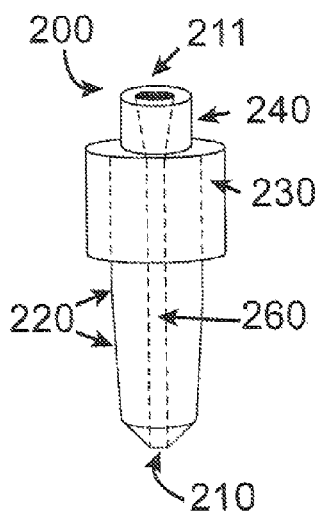
FIGS. 4A and 4D include side views of valve inserts according to certain embodiments of the invention.

Devices and methods to facilitate fluid transmission through valved catheters are disclosed herein. Although physical characteristics of a human body can be measured using elongated tools inserted through valved catheters, this approach risks damaging in-line catheter valves. The systems and methods described herein avoid the risk of valve damage by using an insert that displaces but does not penetrate a valve element.

Examples of medical devices that can be used with the invention include, without limitation, peripherally-inserted central catheters ("PICC's"), central venous catheters ("CVC's"), dialysis catheters and midline infusion catheters that include internal valves. While the examples set forth in this specification focus on implantable catheters for vascular access, the systems and methods of the invention are not limited to vascular devices but are compatible with any medical device having an external valve, including diagnostic and/or interventional catheters and sheaths. Similarly, while the examples set forth herein focus on valves having a flexible diaphragm with one or more slits, the principles of the invention are compatible with a variety of normally-closed pressure activated valve designs.

With reference to the embodiments depicted in FIG. 1, a system 100 according to the invention includes a valve housing 150. The valve housing 150 includes a valve inlet 151, a valve outlet 152, a proximal valve lumen 153 and a distal valve lumen 154. The proximal and distal lumens 153, 154 are separated by a valve element 155 which, in preferred embodiments, is a flexible membrane having at least one slit 156 therethrough. During ordinary valve operation, the edges of the slit 156 remain together, and fluid does not flow, unless a pressure differential thereacross exceeds a predetermined threshold. When a pressure differential across the valve element 155 exceeds the threshold, the membrane deforms so that the edges of the slit 156 separate and fluid flows across the valve from the side with higher pressure to the side with lower pressure.

The system 100 also includes an insert 200, which has a distal insert section 210, a proximal insert end 211, an insert shaft 220, and an insert lumen 260 which extends from the distal insert tip 210 to the proximal insert end 211 and is open to the exterior of the insert in both places. In preferred embodiments, the insert 200 also includes a proximal connector 240 that can be attached to a pressure measurement and/or pressure transduction apparatus, and a proximal external housing 230 that can connect to the valve inlet 151 of the valve housing. Insert shaft 220 is sized to fit within the proximal valve lumen 153 of the valve housing 150. Thus, insert shaft 220 preferably has a maximum outer diameter that is slightly less than a minimum inner diameter of proximal lumen 153. As shown in FIG. 1A, the length 250 of insert shaft 220 preferably corresponds to the length 157 of the proximal valve lumen 153, so that when insert 700 is fully engaged with valve housing 150, as shown in FIGS. 1B and 2B, the distal insert tip 210 of the insert 200 contacts valve element 155 and displaces the flexible membrane it so that the edges of the slit 156 separate from one another. In use, the insert 200 preferably does not penetrate the valve element 155.

In some embodiments, after the insert 200 has been fully engaged with the valve housing 150, the insert lumen 260 is aligned with a gap between edges of the slit 156 so that fluid can flow and pressure can be directly transmitted between the insert lumen 260 and the distal valve lumen 154. As shown in FIG. 2, the opening of the insert lumen 260 at the distal insert tip 210 may be positioned so that, as the insert 200 is inserted into the proximal valve lumen 153 and the distal insert tip 210 approaches the membrane 155, the insert lumen 260 aligns with the slit 156 as shown in FIG. 2A. When the insert 200 is fully engaged with the valve 100, the distal insert tip 210 of the insert presses into the valve element 155, displacing the edges of the slit 156 and creating a fluid communication channel or gap 156' through which fluid can flow between the insert lumen 260 and the distal valve lumen 154.

In some embodiments, however, the opening of the insert lumen 260 is not aligned with the slit 156, and either one or both of the opening of the insert lumen 260 and the slit 156 is offset from the central longitudinal axis of the insert 200 and/or the proximal and distal valve lumens 153, 154. In these embodiments, the distal insert tip 210 presses into the valve element 155, advantageously utilizing the elasticity of the membrane comprising the valve element to stretch and open the slit or slits 156, thereby permitting fluid flow and transmission of fluid pressure across the valve element 155 and between the proximal and distal lumens 153, 154. This in turn permits fluid flow and transmission of fluid pressure between the insert lumen 260 and the distal valve lumen 154.

Figure 5A:
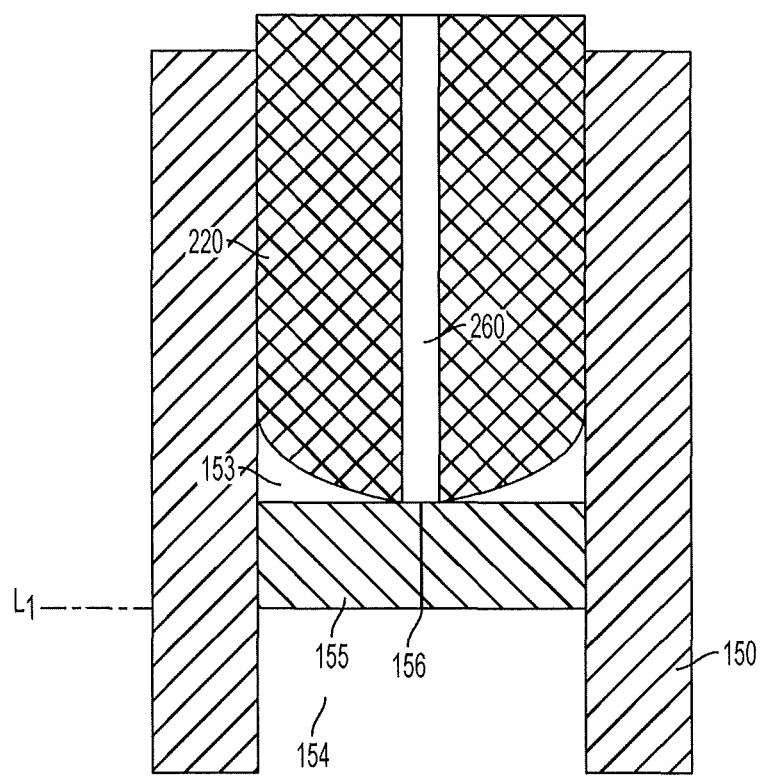
FIGS. 5A and 5B include cross-sectional views of valve inserts and valves according to certain embodiments of the invention.
Figure 5B:
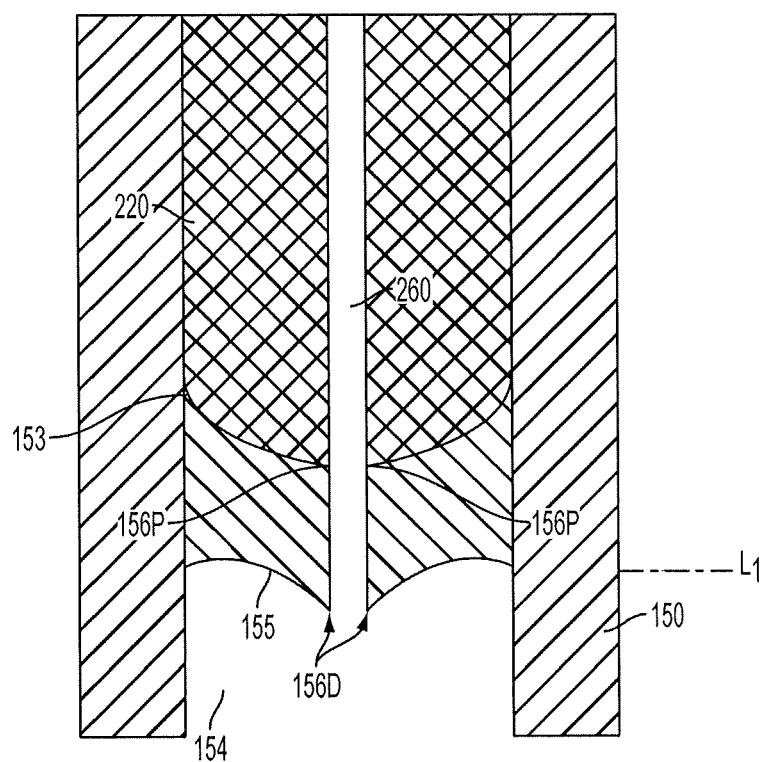

With respect to the insertion of insert 200 into valve housing 150, in preferred embodiments, the insert 200 contacts the valve element 155, but does not penetrate the slit 156. As shown in FIGS. 5A and 5B, the at least one slit 156 has proximal edges 156P which face the proximal valve lumen 153 when the valve element 155 is closed, and distal edges 156D which faces the distal valve lumen 154 when the valve is closed. FIG. 5A shows an insert 200 of the invention positioned in so that it contacts valve element 155 but does not open the slit 156. When the valve is completely closed, the entire distal surface of the valve element 155 is disposed along the plane identified by reference line $L_1$. As the insert 200 is advanced in the valve housing 150, the distal insert tip 210 displaces the edges of the slit 156 downward and outward, such that the distal edge 156D of the slit 156 extend below reference line $L_1$. According to one embodiment, the inert is advanced no further than the position shown in FIG. 5C: the edges of the slit 156 are pressed apart, but at all times the proximal edges 156P remain proximal to the distal edges 156D of the slit 156 extend below reference line $L_1$. Preferably, the insert is advanced no further than the position shown in FIG. 5B. The edges of the slit 156 are pressed apart, but the proximal edges 156P preferably do not extend beyond the plane defined by reference line $L_1$, and remain proximal to the distal edges 156D, thereby minimizing the risk of leakage due to imperfect resealing and/or damage to the valve.

Figure 5C:
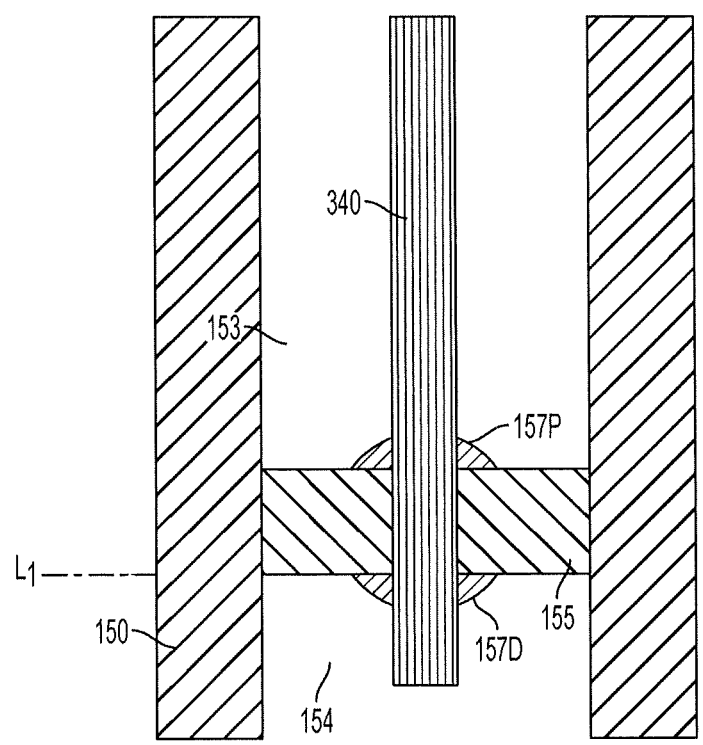
FIG. 5C includes a cross-sectional view of a prior art device.

Inserts of the invention advantageously reduce the risk of leakage due to imperfect resettling and/or valve damage relative to devices disclosed in the prior art, such as the device 340 illustrated in FIG. 5C, in which an elongate member is inserted into and through the slit 156. In the prior art device, the edges of the slit 156 compress against the elongate member 340 and bulge into distorted portions 157P and 156D. Compression and distortion of the edges of the slit 156 in this manner increases the risks of imperfect re-sealing and permanent damage to the valve element.

In some embodiments, the insert 200 includes features to prevent the distal insert tip 200 from advancing too far. For example, the proximal insert connector 240 may include a female luer tip having a threading pattern selected so that, when the proximal insert connector is fully screwed down, it does not extend beyond the position shown in FIG. 5B.

FIG. 3 depicts an insert 200 according to two embodiments of the invention. The embodiment in FIG. 3A-B corresponds to a one-piece valve insert substantially as described above. In the embodiment of FIG. 3C-D, the valve insert 200 includes proximal and distal shafts 221, 222. A spring 270 or, in some embodiments, an elastomeric member is positioned around the junction of the proximal and distal shafts 221, 222, allowing for limited compression and extension of the valve insert about its long axis. The spring 270 preferably has a spring constant that is greater than or equal to that of the flexible membrane comprising the valve element 155 and is chosen to permit the distal insert tip 210 to apply sufficient force to displace the valve element 155 and separate the edges of the slit 156, but not enough to permit the distal insert tip 210 to penetrate the valve element 155. The combined length 250 of the proximal and distal shafts 221, 222 varies depending on the degree of compression, with the length 250 being slightly longer than the length 157 of the proximal valve lumen 153 when the valve insert 200 is not engaged with the valve housing 150, and compressing to fit within the proximal valve lumen 153 when engaged. In certain embodiments, the proximal and distal shafts 221, 222 can be rotated relative to one another. Thus, in embodiments in which the proximal external housing 230 of the valve insert 200 rotates to in over the exterior of the valve inlet 151—for example if the valve inlet 151 includes a male luer end and the proximal external housing 230 includes a female luer end—the proximal shaft 221 can rotate freely with the proximal external housing 230 without translating that rotation to the distal insert tip 210 or the flexible membrane.

To prevent fluid leakage out of the insert lumen 210 at the junction of the proximal and distal shafts 221, 222, one or more compressible sealing members 280, 281 may be utilized as shown in FIG. 3C. Sealing members 280, 281 can be, for example, elastomeric O-rings or any other suitable sealing mechanism known in the art. The sealing member(s) may comprise any suitable material known in the art, including silicone, EPDM, polyurethane, neoprene, FEP, etc. In addition, the insert 200 may be configured to prevent leakage of fluid through the proximal valve lumen 153. In some embodiments, an outer diameter of a portion of the insert 200 which is inserted into the proximal valve lumen 153 is slightly less than the inner diameter of the proximal valve lumen 153, inhibiting or preventing fluid flow around the insert 200. In some embodiments, the proximal external housing 230 of the insert engages with the valve inlet 151 to form a seal that prevents fluid leakage out of the proximal valve lumen 153. In some embodiments, the insert 200 may have an outer diameter chosen to match up with an inner diameter of the lumen, possibly preventing leakage.

Figure 4B:
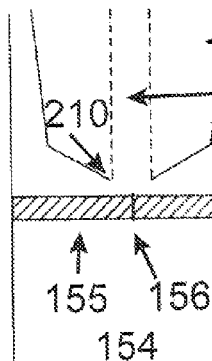
FIGS. 4B, 4C, 4E and 4F include cross sectional views of valve inserts positioned within pressure activated valves according to certain embodiments of the invention.
Figure 4C:
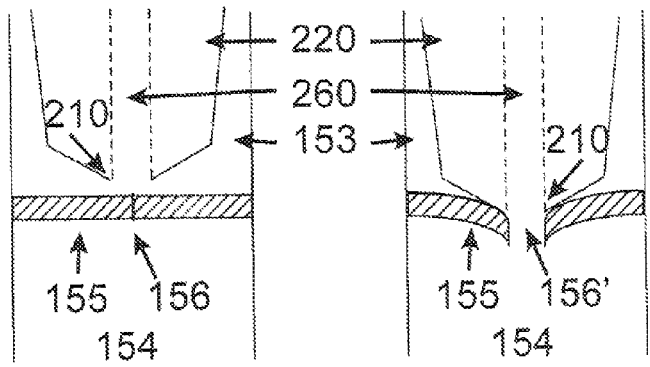
Figure 4D:
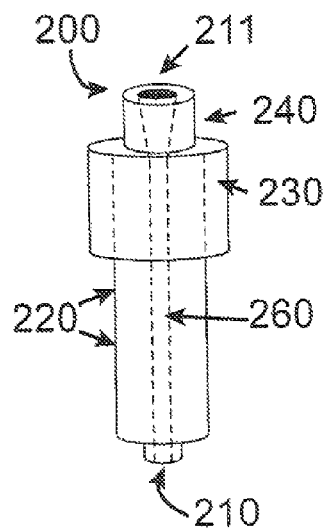
Figure 4E:
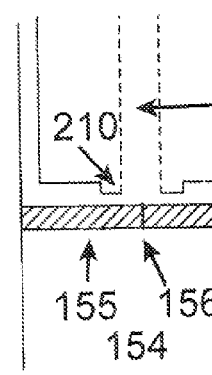
Figure 4F:
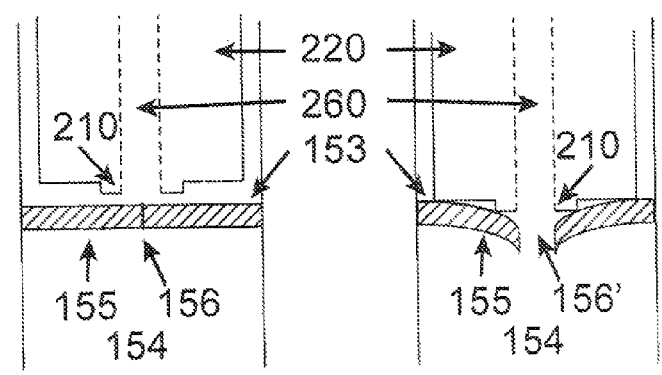

The shape of the distal insert tip 210 is chosen to facilitate proper function of the insert 200 while avoiding damaging the valve element 155. In preferred embodiments, such as the one shown in FIGS. 1-3, the distal tip is gently rounded. In alternate embodiments, the valve has a conical distal insert tip 210, as is shown in FIG. 4A-C, or a stepped distal insert tip 210, as is shown in FIG. 4D-F. The principle of operation remains the same regardless of the tip shape: when the valve insert 200 is fully engaged with the valve housing 150, as shown in FIGS. 4C and F, the tip 210 displaces but does not penetrate the valve element 155 so that the edges of the slit 156 separate, and the insert lumen 260 of the valve insert 200 is placed into fluid communication with the distal valve lumen 154. The insert lumen 260 may open at the distal insert tip 210 in any suitable configuration. In some embodiments, the opening of the insert lumen 260 at the distal insert tip 210 is circular, while in other embodiments, the opening is rectangular, oval shaped, or otherwise generally elongated so as to overlie a slit 156 of the valve element 155, which arrangement may improve fluid flow and transmission of pressures and/or prevent or minimize leakage around the distal insert tip 210. The internal threading 230 and the external threading 151 can be configured to align the rectangular or oval opening along the same lateral axis as the slit.

In some embodiments, the insert 200 facilitates the transmission and/or measurement of a pressure such as a central venous pressure, a V-pressure wave generated by the filling of the right atrium, an A-pressure wave generated by the contraction of the right atrium, or any other pressure caused, directly or indirectly, by a contraction of the heart of a patient which may be desired to be measured. The insert 200 can also facilitate the transmission and/or measurement of acoustic pressure waves such as those caused by the opening and closing of one or more cardiac valves, or acoustic waves caused by an external acoustic generator.

In some embodiments, the insert 200 facilitates the accurate placement of a distal end of a catheter, for example as disclosed in U.S. patent application Ser. No. 12/594,869 by David Ziv, published as Pre-Issue Publication number 2010/0049062, the entire disclosure of which is hereby incorporated by reference for all purposes. Using inserts of the invention, a distal end of a catheter may be located within the vasculature of a patient and/or may be placed in an optimal position for a given application. Positioning of a catheter may be achieved, for example, by measuring a delay time, phase shift, or amplitude of a pressure wave and/or an acoustic wave (or any other wave or signal) transmitted through a catheter and an insert of the invention and/or comparing the measured value to a reference value. More generally, inserts of the invention may be used to facilitate any treatment that includes the measurement of a signal or a substance that is transmitted through the valve of a catheter.

Using inserts of the invention, a catheter may be positioned during an insertion procedure at a desired site. Additionally, inserts of the invention may facilitate the repositioning of catheter tips that have migrated from their initial positions, or which need to be repositioned for other reasons.

Inserts of the invention may be configured to connect to a pressure measurement apparatus, such as a manometer apparatus or a digital pressure transducer system. In certain embodiments, the proximal insert connector 240 comprises a female liter tip that can be connected to and disconnected from a pressure measurement apparatus. In other embodiments, any suitable connector known in the art, including without limitation a threaded or unthreaded male or female luer connector or a barb connector, can be used to facilitate connections to a pressure measurement apparatus. The connections can be either reversible or permanent.

Alternatively, inserts of the invention may include features to facilitate direct pressure sensing, such as an electronic pressure transducer for sensing a fluid pressure within the insert lumen 260, a wire for conducting electrical signals generated by the electronic pressure transducer to a central processor, and/or external valve for removing air from the fluid flow path that includes the insert 200 and the valve housing 150.

Valve inserts of the invention can be used in any application where it is desirable to measure a physical characteristic or signal from a patient across a valve member in a catheter. Valve inserts of the present invention are advantageously used to facilitate measurement of fluid pressure with a valved medical device. In a preferred embodiment, partially illustrated in FIG. 1, an insert 200 is inserted into a valve housing 150 so that the proximal external housing 230 connects to the valve inlet 151 of the valve housing 150 while the distal insert tip 210 engages with the valve element 155 and displaces the edges of the slit 156, placing the lumen 260 of the valve insert 200 in fluid communication with the distal valve lumen 154 of the valve housing 150. In certain embodiments, before insertion into valve housing 150, the valve insert 200 is connected via the proximal connector 240, directly to a pressure measurement apparatus, or to a tube that is connected to a pressure measurement apparatus. A directional stopcock or other fluid control device can also optionally be connected between the insert 200 and the pressure measurement apparatus. After the proximal connector 240 is connected to the pressure measurement apparatus, the entire system is optionally flushed with a fluid solution, so that no air is introduced into the system when the valve insert 200 is inserted into the valve housing 150. After the insert 200 is fully engaged with the valve housing 150, fluid can flow freely and pressure can be equalized through the entire system 100. To verify that the valve insert 200 is correctly inserted, an operator can push fluid through the system, or withdraw fluid from the system 100 and confirm that there is no resistance to fluid flow. An operator can also push or withdraw fluid through the system to purge any air from the system. Pressure measurements can then be taken through system 100.

Another application for valve inserts according to the invention includes transmission of fluid across a normally closed valve for ECG measurement via a column of saline or other transmission fluid. It is common to measure ECG signals from the heart for various clinical applications, such as detection of atrial fibrillation or ECG based tip location. The column of saline runs from the tip of the catheter, such as a PICC line, through to a proximal portion of the catheter, where the ECU signal is measured. The valve insert can be used to bypass the valve using the methods described above, so that the column of saline can be in fluid communication with the proximal ECG measurement element. In addition, the bypass element can itself have an incorporated ECG measurement element, such as an electrode connected to an inner valve insert wall in fluid communication with the lumen, or an electrode connected to a valve insert extension tube or luer.

Valve inserts of the invention can be made using any suitable method known in the art, including without limitation injection molding, extrusion, machining and combinations thereof. Valve inserts of the invention can be made of any suitable material known in the art, including without limitation polycarbonate, nylon, Pelox, polyethylene, polypropylene, FEP, ABS, metals including stainless steel, and other suitable materials, which may be combined in any suitable way. In some embodiments, at least a portion of the insert 200 that includes the tip 210 is made of stainless steel or another suitable metal.

In some embodiments such as those depicted in FIG. 6, the insert includes art extension tube 290, which can be clamped using a clamp 295 in order to prevent flow through the extension tube 290, thereby preventing fluid leakage through the insert 200, for example during insertion into the valve housing 150. In use, insert 200 is inserted into a valve housing 150 with the extension tube 290 clamped shut (FIG. 6B) in order to prevent reflux of blood through the catheter and the insert upon engagement of the insert tip 210 with the valve element 155.

While the examples described herein have focused on inserts having substantially linear insert lumens 260, the insert lumen may be non-linear, and may include branches, etc. Additionally, as shown in FIG. 7, the insert may include one or more outlets at sites other than the distal-most insert tip 210, corresponding to valve membranes having multiple off-set slits.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

Reference throughout this specification to "one example," "an example," "one embodiment," "an embodiment" or "some embodiments" means that a particular feature, structure, or characteristic described in connection with the example is included in at least one example of the present technology. Thus, the occurrences of the phrases "in one example," "in an example," "one embodiment," "an embodiment" or "some embodiments" in various places throughout this specification are not necessarily all referring to the same example. Furthermore, the particular features, structures, routines, steps, or characteristics may be combined in any suitable manner in one or more examples of the technology. Any headings provided herein are for convenience only and are not intended to limit or interpret the scope or meaning of the claimed technology.

Certain embodiments of the present invention have described above. It is, however. expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention.

Variations, modifications, and other implementations of what was described herein will occur to those of ordinary skill in the art without departing from the spirit and the scope of the invention. As such, the invention is not to be defined only by the preceding illustrative description but by the spirit and scope of the following claims.

What is claimed is:

1. A method of measuring a physical characteristic in a patient, the method comprising the steps of:
    placing a catheter with a valve housing within the patient, the valve housing comprising a membrane having at least one slit therethrough;
    placing an insert within the valve housing, the insert comprising:
        a proximal shaft, a distal shaft with a distal tip, a lumen extending therebetween, and a sealing member disposed on an external surface of the insert at a junction of the proximal shaft and the distal shaft, the sealing member preventing leakage into or out of the insert, the proximal shaft and distal shaft configured to rotate independently of one another within the valve housing;
        the distal tip configured to contact the membrane and open, but not penetrate, the at least one slit, thereby placing the insert lumen in fluid communication with a lumen of the valve housing;
    attaching a pressure measurement apparatus to a connector on the proximal shaft; and
    measuring the physical characteristic through a fluid within the lumen of the valve housing and the insert lumen.

2. The method of claim 1, wherein the physical characteristic is selected from the group consisting of a pressure wave, acoustic wave and ECG wave.

3. The method of claim 1, further comprising the step of determining a position of a distal tip of the catheter relative to the membrane based on a measured fluid pressure.

4. The method of claim 3, further comprising the step of repositioning the distal tip of the catheter relative to the membrane.

5. The method of claim 4, wherein the distal tip of the catheter is repositioned to obtain an improved measurement of the physical characteristic.

6. The method of claim 3, further comprising the step of repositioning the distal tip of the catheter.

7. The method of claim 1, further comprising the step of determining a position of a distal tip of the catheter relative to the membrane based on a measured ECG wave.

8. The method of claim 1, wherein the membrane is a pressure activated valve.

9. The method of claim 1, wherein the at least one slit is configured to open in response to a fluid pressure in excess of a predetermined threshold.

10. A method of measuring a physical characteristic of a patient, comprising the steps of:
    placing a medical device within a patient, the medical device comprising an insert disposed within a housing;
    the housing comprising a valve having at least one slit therethrough;
    the insert comprising:
        a proximal shaft,
        a distal shaft with a distal tip,
        a lumen extending therebetween, and
        a sealing member disposed on an external surface of the insert at a junction of the proximal shaft and the distal shaft, the sealing member preventing leakage into or out of the insert,
        the proximal shaft and distal shaft configured to rotate independently of one another within the housing;
        the distal tip configured to contact the valve and open, but not penetrate, the at least one slit, thereby placing the insert lumen in fluid communication with a lumen of the housing,
    attaching a pressure measurement apparatus to the proximal shaft; and
    measuring the physical characteristic through a fluid within the lumen of the valve housing and the insert lumen.

11. The method of claim 10, wherein the valve is a pressure activated valve.

12. The method of claim 10, wherein the at least one slit is configured to open in response to a fluid pressure in excess of a predetermined threshold.

* * * * *